United States Patent
Herleikson

(10) Patent No.: US 6,567,698 B2
(45) Date of Patent: May 20, 2003

(54) SYSTEM AND METHOD FOR APPLYING SEQUENTIAL LOW ENERGY DEFIBRILLATION PULSES

(75) Inventor: Earl C. Herleikson, Lebanon, ME (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/908,143

(22) Filed: Jul. 17, 2001

(65) Prior Publication Data

US 2003/0018361 A1 Jan. 23, 2003

(51) Int. Cl.$^7$ .................................................. A61N 1/39
(52) U.S. Cl. ............................................................ 607/5
(58) Field of Search ......................................... 607/4, 5

(56) References Cited

U.S. PATENT DOCUMENTS

| | | | |
|---|---|---|---|
| 3,241,555 A | 3/1966 | Caywood et al. | 128/421 |
| 4,559,946 A | * 12/1985 | Mower | |
| 4,708,145 A | 11/1987 | Tacker, Jr. et al. | 128/419 |
| 4,727,877 A | 3/1988 | Kallok | 128/419 |
| 4,996,984 A | 3/1991 | Sweeney | 128/419 |
| 5,107,834 A | 4/1992 | Ideker et al. | 128/419 |
| 5,163,427 A | 11/1992 | Keimel | 128/419 |
| 5,306,291 A | 4/1994 | Kroll et al. | 607/5 |
| 5,366,485 A | 11/1994 | Kroll et al. | 607/5 |
| 5,383,907 A | 1/1995 | Kroll | 607/5 |
| 5,441,518 A | 8/1995 | Adams et al. | 607/5 |
| 5,522,853 A | 6/1996 | Kroll | 607/5 |
| 5,817,132 A | * 10/1998 | Karagueuzian | |
| 5,978,705 A | 11/1999 | KenKnight et al. | 607/5 |
| 6,085,116 A | 7/2000 | Pendekanti et al. | 607/5 |
| 6,091,989 A | 7/2000 | Swerdlow et al. | 607/5 |
| 6,141,584 A | 10/2000 | Rockwell et al. | 607/5 |

FOREIGN PATENT DOCUMENTS

| | | | |
|---|---|---|---|
| WO | WO0139833 | 7/2001 | A61N/1/39 |

OTHER PUBLICATIONS

"A Three–Dimensional Finite Element Model of Human Transthoracic Defibrillation: Paddle Placement and Size," by Camacho, Lehr and Eisenberg, IEEE Transactions on Biomedical Engineering, Jun. 1995.

"Current Concepts for Selecting the Location, Size and Shape of Defibrillation Electrodes" by Ideker, Wolf, Alferness, Krassow ska and Smith, Pace, 1991.

* cited by examiner

Primary Examiner—Scott M. Getzow

(57) ABSTRACT

A transthoracic electrical defibrillation method and apparatus for effectively defibrillating a fibrillating heart by delivering successive low energy electrical shocks to the fibrillating heart with the second such shock being applied at the onset of reinitiate fibrillation. Such low energy shocks produce current densities of sufficient magnitude to simultaneously place only a portion of myocardial cells in a refractory state, that portion being less than that necessary to defibrillate the heart. The composite effect of two or more low energy shocks each applied synchronously with the initiation or reinitiation of fibrillation, results in the successful defibrillation of a fibrillating heart.

20 Claims, 6 Drawing Sheets

SYSTEM AND METHOD FOR APPLYING SEQUENTIAL LOW ENERGY DEFIBRILLATION PULSES

BACKGROUND OF THE INVENTION

1. Field of the Invention

The present invention relates generally to electrotherapy devices and, more particularly, to an electrotherapy device that applies sequentially low energy current pulses for improved defibrillation efficacy.

2. Related Art

External defibrillators are used to provide electrical shocks to treat patients for a variety of heart arrhythmia such as ventricle fibrillation. Ventricle fibrillation is an uncoordinated contraction and relaxation of the individual fibers of the heart that produces no blood flow and results in death unless corrective measures are applied within minutes of onset. The most widely accepted clinical procedure to reverse the life-threatening condition of ventricular fibrillation is transthoracic electrical defibrillation in which an electrical pulse is applied to the surface of the thorax through electrodes, commonly called paddles or pads.

The use of electrical shocks to terminate ventricular fibrillation entails passing electrical current through the myocardium so as to restore the heart to its natural heart rhythm. For example, external defibrillators such as portable automatic or semi-automatic external defibrillators (generally, AEDs), typically provide a single, high-energy shock to a fibrillating patient through a pair of electrodes attached to the patient's torso. If successful, the shock converts ventricular fibrillation to a normal sinus rhythm. However, the energy that must be delivered with the electrical shock to achieve defibrillation can produce deleterious effects, ranging from transient conduction abnormalities to myocardial necrosis. This is particularly true for pediatric patients whose body mass is a fraction of the typical adult patient.

Generally, manual external defibrillators are configured by a trained operator for the particular patient and patient condition, including the energy level to be delivered by the electrical shock. In contrast, automatic external defibrillators make such determinations for the device operator by using a fixed energy or escalating defibrillation energy protocol. Many of today's AEDs also adjust varius aspects of the defibrillation waveform (such as time duration) based on patient impedance. Such an impedance measurement may provide useful information for certain purposes such as to estimate the impedance of the entire defibrillator path, heart rate, respiratory rate and other physiological parameters. However, such an approach fails to provide the information necessary to make an accurate estimation of patient size and mass. As a result AEDs often generate a single shock that may be optimal for larger adult patients but potentially damaging to smaller patients. Most AEDs today are not qualified for use on pediatric patients for this reason.

What is needed, therefore, is a system and method that can effectively defibrillate patients of varying body mass automatically and without a trained operator's intervention.

SUMMARY OF THE INVENTION

The present invention provides a transthoracic electrical defibrillation method and apparatus for effectively defibrillating a fibrillating heart by delivering successive low energy electrical shocks to the fibrillating heart with the second such shock being applied at the onset of reinitiate fibrillation. Such low energy shocks produce current densities of sufficient magnitude to simultaneously place only a portion of myocardial cells in a refractory state, that portion being less than that necessary to defibrillate the heart. The composite effect of two or more low energy shocks each applied synchronously with the initiation or reinitiation of fibrillation, results in the successful defibrillation of a fibrillating heart.

Specifically, application of a first low energy shock induces a current density sufficient to depolarize a portion of the myocardial cells, this portion being typically less than that necessary to enable the myocardium to return to a normal sinus rhythm. In response to the first shock, then, some cells depolarize and enter a refractory state while other cells do not depolarize and remain non-refractory.

The polarization charge of those cells that remain non-refractory despite the first current pulse varies from cell to cell. This residual charge that remains in a cell membrane can subsequently cause the cell to depolarize. This spontaneous depolarization of such partially stimulated cells is referred to as reinitiate fibrillation. That is, fibrillation activity will reinitialize subsequent to the application of the first low energy pulse due to the depolarization of cells that received lower defibrillation current densities. These cells will depolarize on their own within a relatively short time after the defibrillation pulse and become refractory.

At the onset of such ECG activity, a second low energy electrical shock is administered. This second low energy shock will maintain the initially depolarized cells in their refractory state. Some of the initially depolarized cells will have yet to begin to repolarize prior to application of the second shock. Those cells will be maintained in their refractory state in response to the second shock. Any initially-depolarized cells that do begin to repolarize after the first shock will depolarize once again in response to the second shock. In addition, the second shock will possibly depolarize additional cells that have since attained a convertible current density. This depolarization will occur synchronously with the depolarization of the lower current density cells that depolarized spontaneously, marking the beginning of reinitiate defibrillation. The cells that are in the refractory state in response to the sequential pulses, in combination with the naturally depolarizing cells, form a critical mass of refractory myocardial cells, enabling the heart to return to a normal sinus rhythm.

Thus, by applying a subsequent low energy pulse to coincide with the first signs of is fibrillation, the sequential pulses of the present invention place the myocardium in a state in which it can respond to a normal sinus rhythm without the myocardial cells attaining current densities of the magnitude produced by conventional defibrillation pulse. That is, by taking advantage of the heart's propensity to reinitialize fibrillation, the present invention supplies sufficient energy to achieve defibrillation while minimizing the peak current applied to the myocardium. This reduces the likelihood of the numerous adverse effects of high current densities. For example, the likelihood of myocardial necrosis decreases, increasing the probability of patient survival. In addition, it may be feasible that patients of all sizes may be defibrillated using one or more low energy current pulses that are safe and effective for all patients from pediatrics to adults. This would enable an AED to implement a single shock protocol that optimally defibrillates all patients. Furthermore, such lower energy currents result in lower applied voltages that can reduce size, weight and cost of the implementing external defibrillator.

A number of aspects of the invention are summarized below, along with different embodiments that may be implemented for each of the summarized aspects. It should be understood that the summarized embodiments are not necessarily inclusive or exclusive of each other and may be combined in any manner in connection with the same or different aspects that is non-conflicting and otherwise possible. These disclosed aspects of the invention, which are directed primarily to systems, methods, data and techniques related to the effective defibrillation, are exemplary aspects only and are also to be considered non-limiting.

In one aspect of the invention a method for defibrillating a fibrillating heart is disclosed. The method includes applying a first low energy current pulse to the heart; detecting a reinitiate fibrillation of the heart subsequent to the application of the first low energy current pulse; and applying, at the onset of reinitiate fibrillation, a second low energy current pulse. Preferably, the method also includes detecting a reinitiate fibrillation of the heart subsequent to the application of the second low energy current pulse; and applying, at the onset of reinitiate fibrillation, a third low energy current pulse.

In another aspect of the invention, an external defibrillator to defibrillate a patient's fibrillating heart is disclosed. The external defibrillator includes an energy delivery system constructed and arranged to deliver sequentially two or more low energy electric shocks to a patient through at least two electrodes applied to the patient; a patient monitoring circuit constructed and arranged to monitor the patient's heart rhythm; and a controller that determines whether the heart is fibrillating and that causes the energy delivery system to apply a first low energy electric shock upon detection of an initial fibrillation, and to apply a second low energy electric shock upon detection of a reinitiate fibrillation.

In a further aspect of the invention a transthoracic electrical defibrillation system is disclosed. The transthoracic electrical defibrillation system effectively defibrillates a fibrillating heart by delivering two successive low energy electrical shocks to the fibrillating heart with the second such low energy shock being applied at the onset of reinitiate fibrillation.

Various embodiments of the present invention provide certain advantages and overcome certain drawbacks of conventional defibrillation techniques. Not all embodiments of the invention share the same advantages and those that do may not share them under all circumstances. This being the, the present invention provides numerous advantages including the noted advantage that patients of all sizes may be defibrillated using one or more low energy current pulses that are safe and effective for all patients from pediatrics to adults. These and other features and advantages of the present invention as well as the structure and operation of various embodiments of the present invention are described in detail below with reference to the accompanying drawings.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps, in which the left-most one or two numerals of a reference numeral indicate the number of the figure in which the referenced element first appears, and in which.

DETAILED DESCRIPTION

Figure 1A:
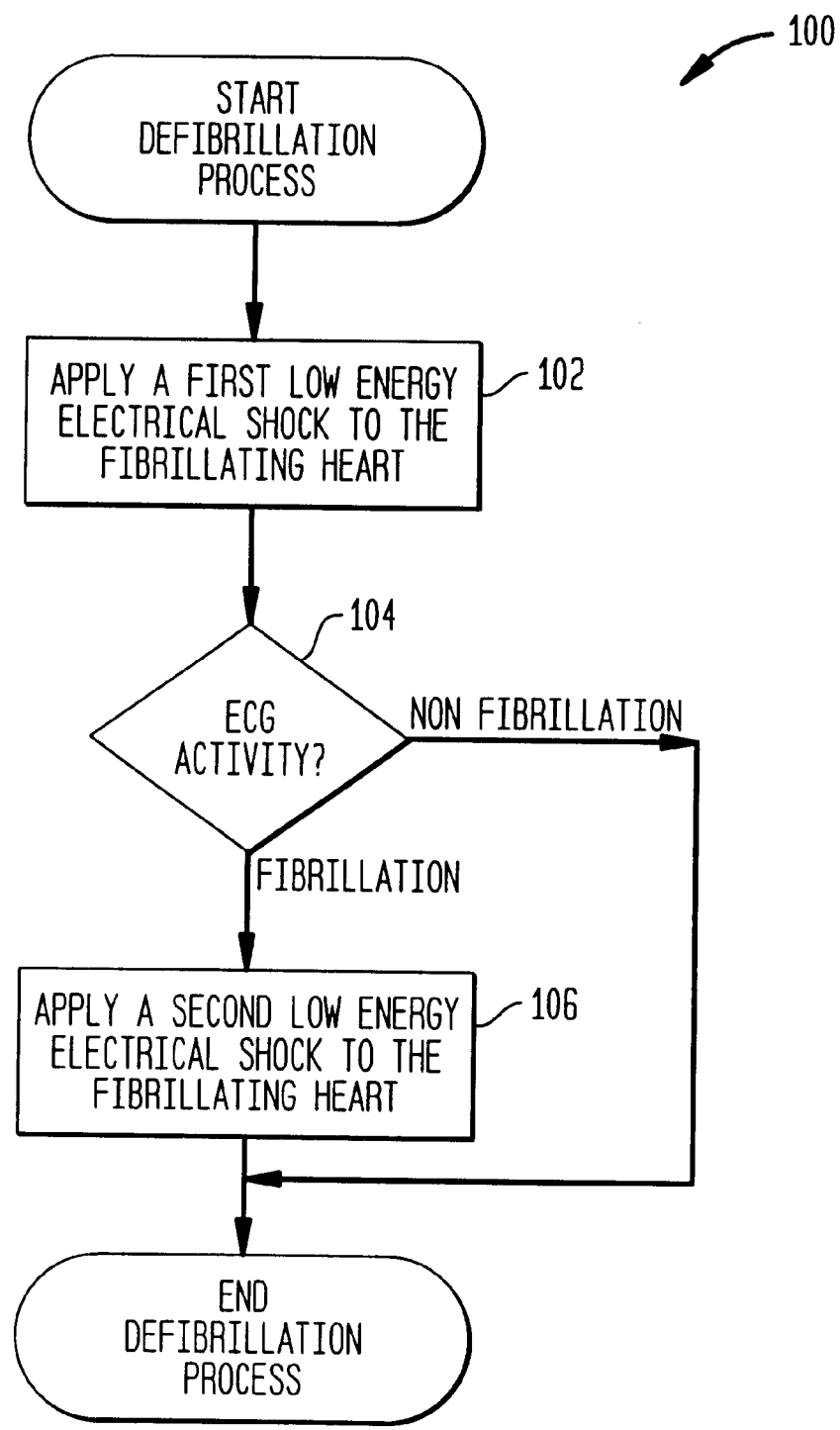
FIGS. 1A and 1B are flow charts of different embodiments of the low energy defibrillation method of the present invention.

Normal myocardial cells have a voltage difference across the cell boundary of approximately 90 mv. When myocardial cells are electrically stimulated and activated, the electrical polarization caused by the normal voltage difference between the inside and outside of the cells collapses and the myocardium is said to "depolarize." Depolarized myocardial cells are referred to as being in a refractory state. Refractory cells will not produce a new activation in response to a further intrinsic or extrinsic electrical stimulus. After depolarization, heart cells begin to re-establish the normal voltage difference. This process is referred to as "repolarization". It may take several hundred milliseconds for the cells to complete the repolarization process. Myocardial cells that have been afforded an adequate length of time to re-establish a sufficiently large voltage polarization are thereafter susceptible to depolarization. Such myocardial cells are referred to as being "nonrefractory". The time interval which is required after a cell has been depolarized until it is again nonrefractory is called the refractory period.

The collapse of a cell's voltage polarization is capable of activating neighboring cells. These nearby cells, in turn, lose their voltage polarization and stimulate still other neighboring cells. In this manner, depolarization activity can propagate throughout the heart. At any given instant, the locations where myocardial cells are depolarizing are called depolarization wavefronts. As depolarization wavefronts move through the heart they convert non-refractory cells to refractory cells which subsequently repolarize and become nonrefractory, as noted above. In a fibrillating heart, depolarization wavefronts move through the myocardium in a chaotic manner. At an instant in time during fibrillation, there will be cells at all possible polarization states, preventing the organized activation of the myocardium to effect blood pumping.

The most widely accepted clinical procedure to reverse the life-threatening condition of ventricular fibrillation is transthoracic electrical defibrillation in which an electrical pulse is applied to the surface of the thorax through electrodes, commonly called paddles or pads. Since a defibrillation shock is experienced by all myocardial cells at the same time, different myocardial cells experience the shock at different relative timing in their electrical cycle. Defibrillation occurs when this pulse produces current densities of sufficient magnitude to simultaneously render a critical mass of myocardial cells refractory. However, the requisite energy to be delivered by the electrical shock to achieve such a widespread current density can produce deleterious effects, ranging from transient conduction abnormalities to myocardial necrosis. A typical AED is designed to achieve successful defibrillation of most all patients with a single shock level. This shock energy level can significantly exceed the required current densities for smaller patients, further increasing the probability of deleterious effects.

The present invention provides a transthoracic electrical defibrillation method and apparatus for effectively defibrillating a fibrillating heart by delivering successive low energy electrical shocks to the fibrillating heart with the second such shock being applied at the onset of reinitiate fibrillation. Such low energy shocks produce current densities of sufficient magnitude to simultaneously place only a portion of myocardial cells in a refractory state, that portion being less than that necessary to defibrillate the heart. The composite effect of two or more low energy shocks each applied synchronously with the initiation or reinitiation of fibrillation, results in the successful defibrillation of a fibrillating heart.

Specifically, application of a first low energy shock induces a current density sufficient to depolarize a portion of the myocardial cells, this portion being typically less than that necessary to enable the myocardium to return to a normal sinus rhythm. In response to the first shock, then, some cells depolarize and enter a refractory state while other cells do not depolarize and remain non-refractory.

The polarization charge of those cells that remain non-refractory despite the first current pulse varies from cell to cell. This residual charge that remains in a cell membrane can subsequently cause the cell to depolarize. These cells will be the first to repolarize to a level that can result in spontaneous depolarization which is referred to as reinitiate fibrillation. That is, fibrillation activity will reinitialize subsequent to the application of the first low energy pulse due to the subsequent depolarization of lower current density cells to their natural refractory state.

At the onset of such ECG activity, a second low energy electrical shock is administered. This second low energy shock will maintain the initially depolarized cells in their refractory state. Some of the initially depolarized cells will have yet to begin to repolarize prior to application of the second shock. Those cells will be maintained in their refractory state in response to the second shock. Any initially-depolarized cells that do begin to repolarize after the first shock will depolarize once again in response to the second shock. In addition, the second shock will possibly depolarize additional cells that have since attained a convertible state. This depolarization will occur synchronously with the depolarization of the lower current density cells that depolarized spontaneously, marking the beginning of reinitiate defibrillation. The cells that are in the refractory state in response to the sequential pulses, in combination with the naturally depolarizing cells, form a critical mass of refractory myocardial cells, enabling the heart to return to a normal sinus rhythm.

Thus, by applying a subsequent low energy pulse to coincide with the first signs of fibrillation, the sequential pulses of the present invention place the myocardium in a state in which it can respond to a normal sinus rhythm without the myocardial cells attaining current densities of the magnitude produced by conventional defibrillation pulse. That is, by taking advantage of the heart's propensity to reinitialize fibrillation, the present invention supplies sufficient energy to achieve defibrillation while minimizing the peak current applied to the myocardium. This reduces the likelihood of the numerous adverse effects of high current densities. For example, the likelihood of myocardial necrosis decreases, increasing the probability of patient survival. In addition, it may be feasible that patients of all sizes may be defibrillated using one or more low energy current pulses that are safe and effective for all patients from pediatrics to adults. This would enable an AED to implement a single shock protocol that optimally defibrillates all patients. Furthermore, such lower energy currents result in lower applied voltages that can reduce size, weight and cost of the implementing external defibrillator.

Figure 1B:
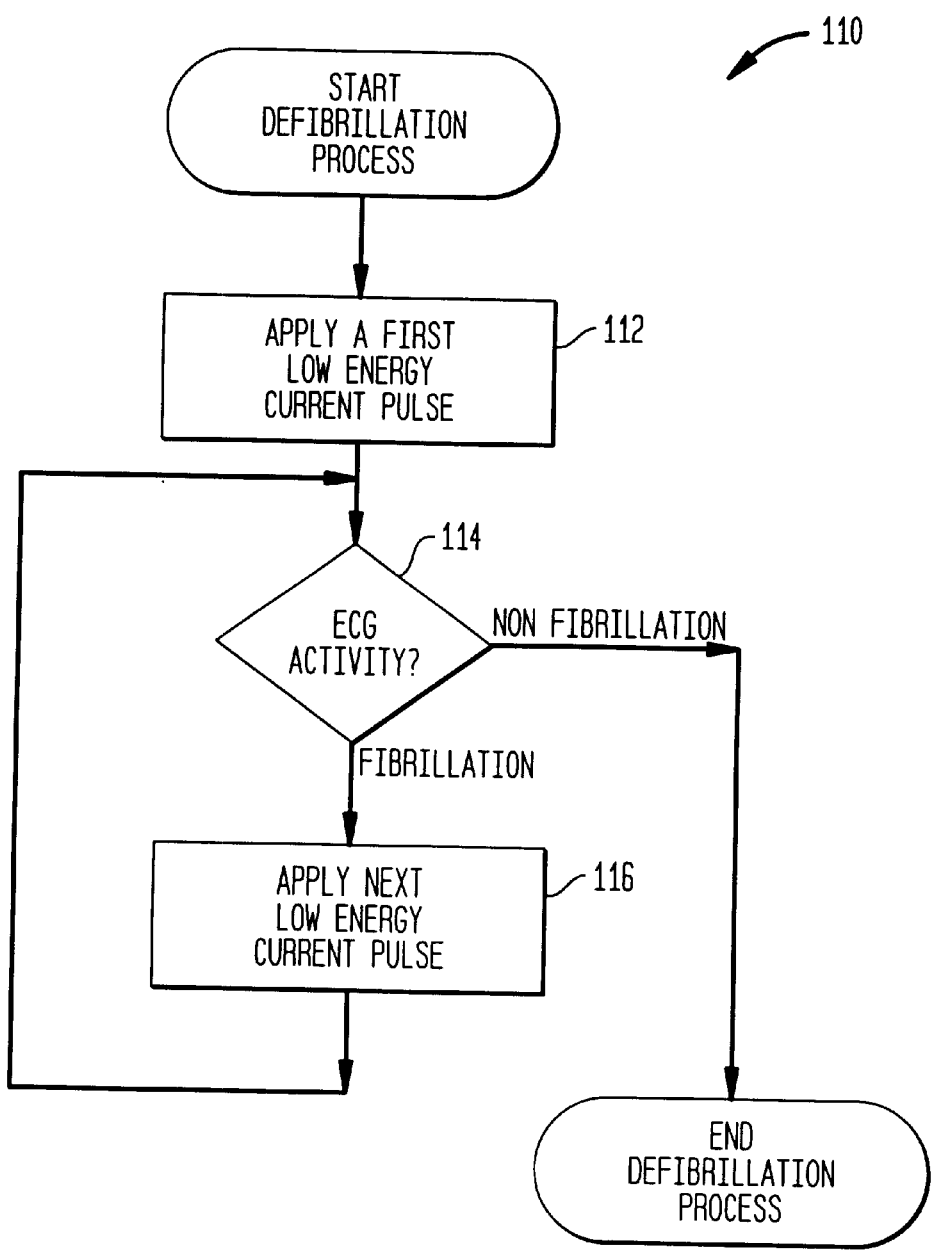

Exemplary implementations of the present invention are illustrated in FIGS. 1A and 1B. Referring to FIG. 1A, a first low energy pulse is applied at block 102 and the heart is monitored at block 104. Upon detection of a fibrillatory event, the second low energy shock is applied at block 106. If the ECG activity after the first shock indicates a non-fibrillation condition, then the patient responded favorably to the first shock alone and should not be shocked a second time. Such a patient may be, for example, a child.

In alternative embodiments such as that shown in FIG. 1B, the present invention applies multiple low energy shocks, each in response to the detection of a fibrillatory event. After the second shock is applied, the patient's ECG activity is once again monitored. Should the patient fibrillate once again, a third pulse is applied and the heart is monitored once again. This process can be repeated any number of predetermined times until a non-fibrillation ECG activity is detected at block 114. The non-fibrillation ECG activity is identified by sufficient time delay between the shock and the first sign of ECG activity.

In further embodiments, other factors may be considered when determining whether to apply an additional shock to the patient. For example, the iterations illustrated in FIG. 1B can be repeated until a certain number of low energy pulses have been delivered.

Figure 2:
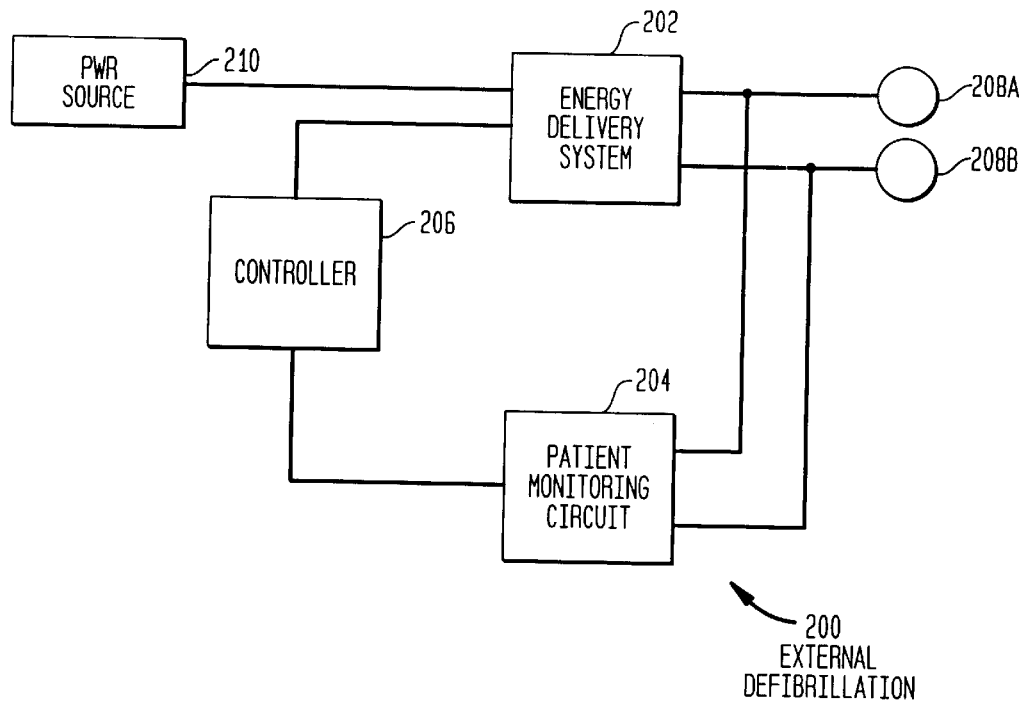
FIG. 2 is a simplified block diagram of an exemplary electrotherapy device configured to deliver sequential low energy defibrillating pulses in accordance with one embodiment of the present invention.

Aspects and embodiments of the present invention will be described herein with reference to an exemplary electrotherapy device. A simplified block diagram of an external defibrillator suitable for incorporating the present invention is illustrated in FIG. 2. External defibrillator 200 includes the necessary components to defibrillate a patient in accordance with the present invention. It should be appreciated that since such external defibrillators are well known in the art, the components described herein and illustrated in FIG. 2 are limited to those implementing functions of the present invention. In the following description it is envisioned that external defibrillator 200 is a portable external defibrillator such as an AED.

Components of external defibrillator 200 operate under the control of a controller 206. Controller 206 may be embodied in a microprocessor, gate array, ASIC, or other control logic architecture, as well as any combination thereof. Preferably, controller 206 is implemented in software code that is executed on a commercially available microprocessor. Generally, such software code is stored in a memory device (not shown) accessible by the microprocessor. As will be described in detail below, controller 206 controls the other components of defibrillator 200 to implement the teachings of the present invention.

External defibrillator 200 includes an energy delivery system 202 that delivers energy to a patient (not shown). Energy delivery system 202 is connected to two electrodes 208A, 208B and a power source 210. In response to controller 206, energy delivery system 104 delivers a sequence of low energy electric shocks to electrodes 208 that are placed in various predetermined locations on the patient. There are many embodiments of energy delivery system 202 that can be implemented. One such exemplary embodiment of energy delivery system 202 is described in detail below.

Patient monitor circuit 204 monitors the patient's heart rhythm and determines whether the heart is fibrillating. Patient monitor circuit 204 receives information, in this embodiment, from sensors integrated in defibrillating electrodes 208. Patient monitor 204 provides controller 206 with a digitized ECG signal that is processed by controller 206 to control energy delivery system 202 in accordance with the teachings of the present invention. Patient monitoring circuit 204 has a dynamic range sufficient to measure with high resolution, and is capable of recovering quickly following a defibrillation event. Patient monitoring circuit 204 is also described in detail below.

Certain of the above and other device components not specifically described in this application may be included and configured to operate in the manner described in U.S. Pat. No. 5,607,454 to Cameron et al., entitled "Electrotherapy Method and Apparatus," the disclosure of which is incorporated herein by reference herein in its entirety.

Figure 3:
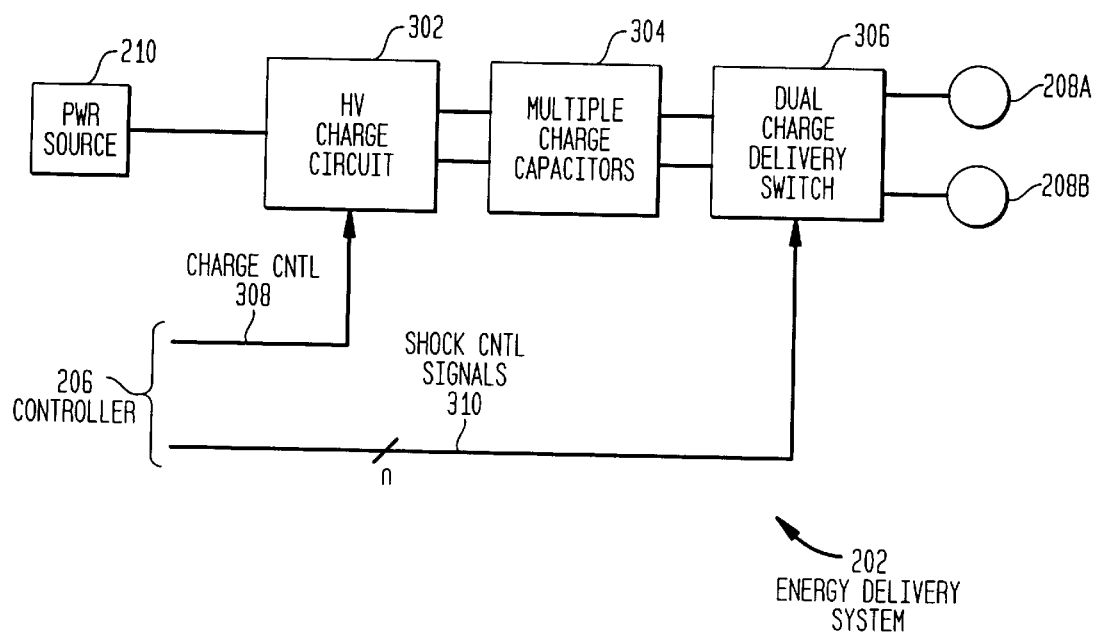
FIG. 3 is a high-level block diagram of one embodiment of the energy delivery system of the present invention.
Figure 4:
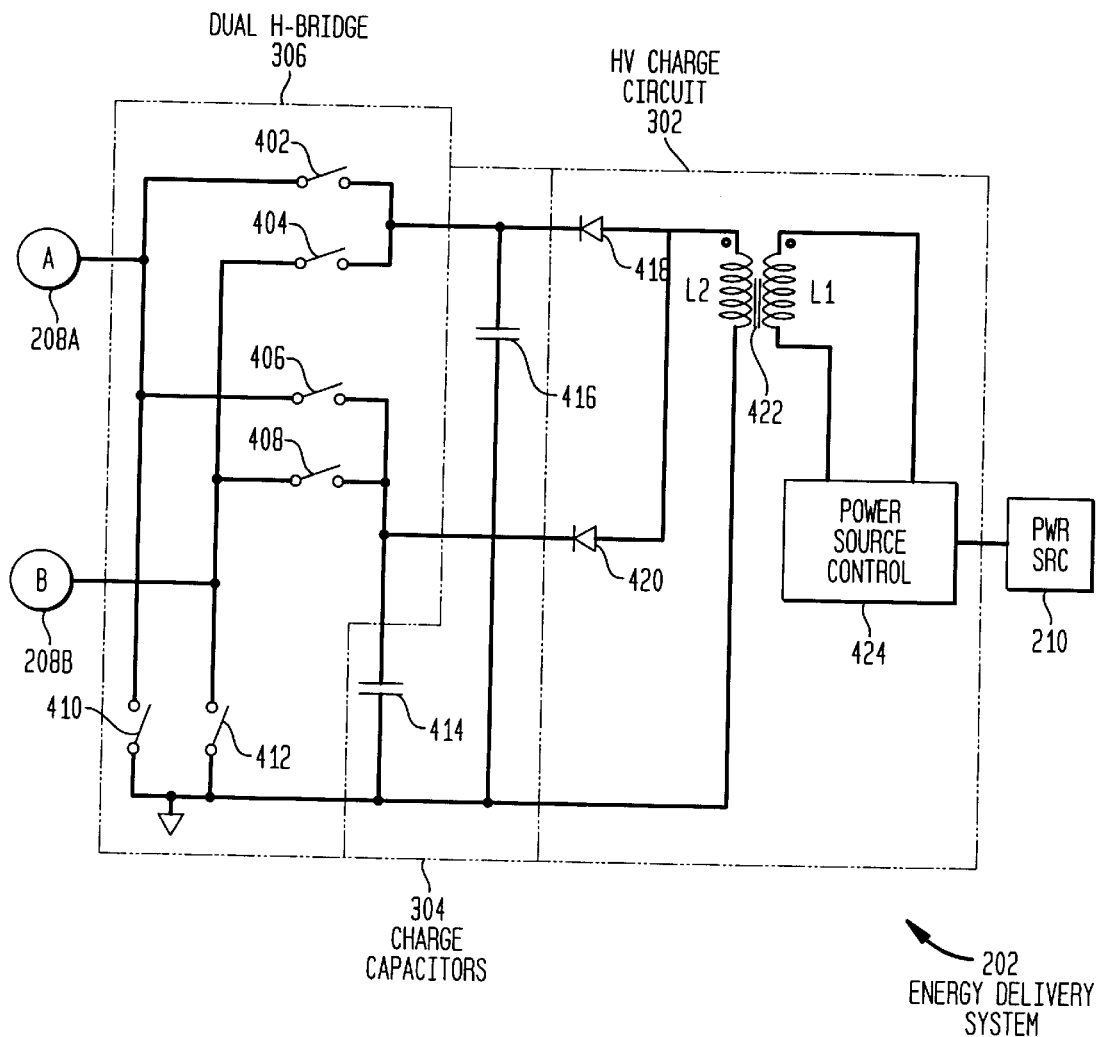
FIG. 4 is a schematic diagram of the energy delivery system illustrated in FIG. 3 in accordance with one embodiment of the present invention.

FIG. 3 is a high-level functional block diagram of energy delivery system 202 in accordance with one embodiment of the present invention. FIG. 4 is a schematic block diagram of one implementation of energy delivery system 202. As noted, energy delivery system 202 administers successive low energy shocks to the patient in response to commands generated by controller 206. In the illustrative embodiment, energy delivery system 202 is constructed and arranged to deliver two such low energy pulses in succession.

Energy delivery system 202 includes a high voltage (HV) charge circuit 302 that receives power from power source 210 and charges multiple charge capacitors 304. HV charge circuit 302 charges capacitors 304 in response to charge control commands 308 generated by controller 206. Charge capacitors 304 includes a plurality of capacitors or banks of capacitors to store the energy to be delivered during each such low energy shock. The independent delivery of energy stored in such capacitors is controlled by multiple charge delivery switch 306. Multiple charge delivery switch 306 delivers independent current pulses to defibrillator paddles 208 in response to a shock control signals 310.

Referring now to FIG. 4, HV charge circuit 302 includes a transformer 422 with a primary coil L1 connected to a power source control circuit 424. Power source control circuit 424 is connected to a power module 210 such as a battery that serves as a source of DC current. Power source control 424 can be any well known power switch circuitry now or later developed that provides an alternating current across L1 of transformer 422. Typically, such power source control circuit includes a FET switch to ground that applies a current pulse to coil L1 of transformer 422.

Connected across the secondary coil L2 of transformer 422 are two high voltage defibrillation capacitors 414 and 416. The positive terminal of secondary coil L2 is connected to capacitors 414 and 416 through diodes 420 and 418, respectively. The alternating current generated at L2 is rectified by diodes 418 and 420, resulting in a series of positive current pulses being applied to capacitors 414, 416. Such current pulses cause energy to accumulate in capacitors 414, 416, as is well known in the art. As noted, in this illustrative embodiment, electrotherapy device 100 applies two successive low energy current pulses to a fibrillating patient. Due to the large amount of energy that must be accumulated in such high voltage capacitors, a relatively long period of time is required to chare capacitors 414, 416. In this illustrative embodiment, a single capacitor is utilized to deliver each low energy pulse of a sequence of such low energy charge pulses. It should be understood, however, that in alternative embodiments a single capacitor could be used to deliver both sequential low energy shocks. In such embodiments, each shock is achieved by partially discharging the one capacitor and/or by rapidly charging the one capacitor in a short enough time for the second shock. It should also be appreciated that in this exemplary description, a single capacitor 414, 416 is used to deliver each low energy shock. In alternative embodiments, each capacitor 414, 416 is replaced with two or more physically separate capacitors electrically connected in series or parallel to produce an equivalent capacitance represented by capacitors 414, 416.

The energy delivered during each current pulse is determined by the capacity of each to capacitor 414,416, the discharge times and patient impedance. In the implementation shown in FIG. 4, capacitors 414, 416 are charged simultaneously and have the same capacity of 100 $\mu f$. If discharged in the same manner, the resulting first and second low energy pulses will deliver the same energy. As one or ordinary skill in the art would appreciate, the energy delivered by the current pulses generated by the present invention need not be the same and can be adjusted dynamically. For example, in one alternative embodiment, capacitors 414, 416 have different capacities resulting in low energy pulses of different energy. In another embodiment, the positive current pulses supplied by transformer 422 are controlled via a simple switch network to control the charging of capacitors 414, 416. In still other embodiments, multiple charge delivery circuit 306 controls the discharge of each capacitor to provide a defibrillation shock with different energy.

As noted, multiple charge delivery switch 306 connects individual capacitors 304 to defibrillation electrodes 208 in response to one or more shock control signals 310 generated by controller 206. In the embodiment illustrated in FIG. 5, multiple charge delivery switch 306 is implemented as a two H-bridges each electrically connecting a capacitor 414, 416 to defibrillation electrodes 208. To reduce cost and complexity, certain switches are included in both H-bridges, as described next below.

One H-bridge includes switches 402, 404, 410 and 412 to control the electrical connection between capacitor 416 and defibrillation electrodes 208. Similarly, the second H-bridge includes switches 406, 408, 410 and 412 to control the electrical connection between capacitor 414 and defibrillation electrodes 208. It should be understood that dual H-bridge 306 can be controlled to apply, for example, monophasic or biphasic pulses to defibrillation electrodes. For example, in one embodiment, the first and the second low energy pulses applied by energy delivery system 202 in accordance with the present invention are biphasic pulses. To apply a biphasic pulse from capacitor 416 to electrodes 208, switches 402 and 412 are closed and switches 404 and 410 are opened. This connects electrode 208A to capacitor 416 and electrode 208B to ground. Then, to reverse the polarity, switches 402 and 412 are opened and switches 404 and 410 are closed to connect electrode 208A to ground and electrode 208B to capacitor 416. It should be understood that similar switching operations are performed by multiple charge delivery circuit 306 to apply a biphasic pulse using capacitor 414. That is, switches 406 and 412 are closed and switches 408 and 410 are opened to connect electrode 208A to capacitor 414 and electrode 208B to ground for the first phase of the biphasic pulse. Then, to reverse the polarity, switches 406 and 412 are opened and switches 408 and 410 are closed to connect electrode 208A to ground and electrode 208B to capacitor 414.

Figure 5:
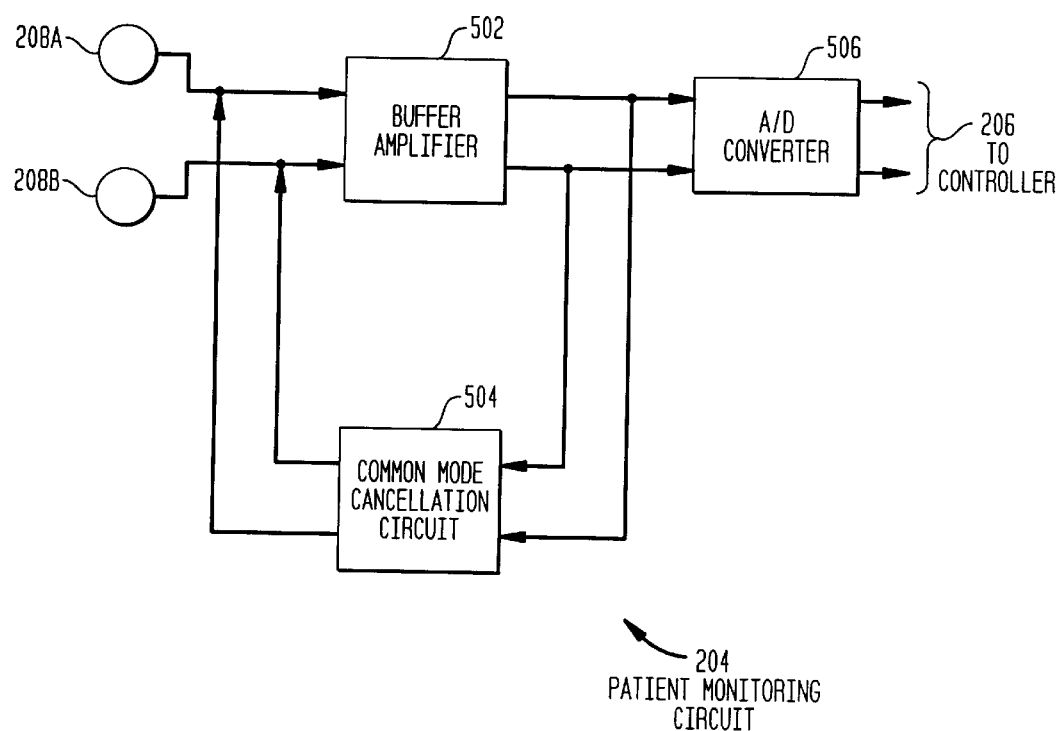
FIG. 5 is a functional block diagram of one embodiment of patient monitoring circuit illustrated in FIG. 2.
Figure 6:
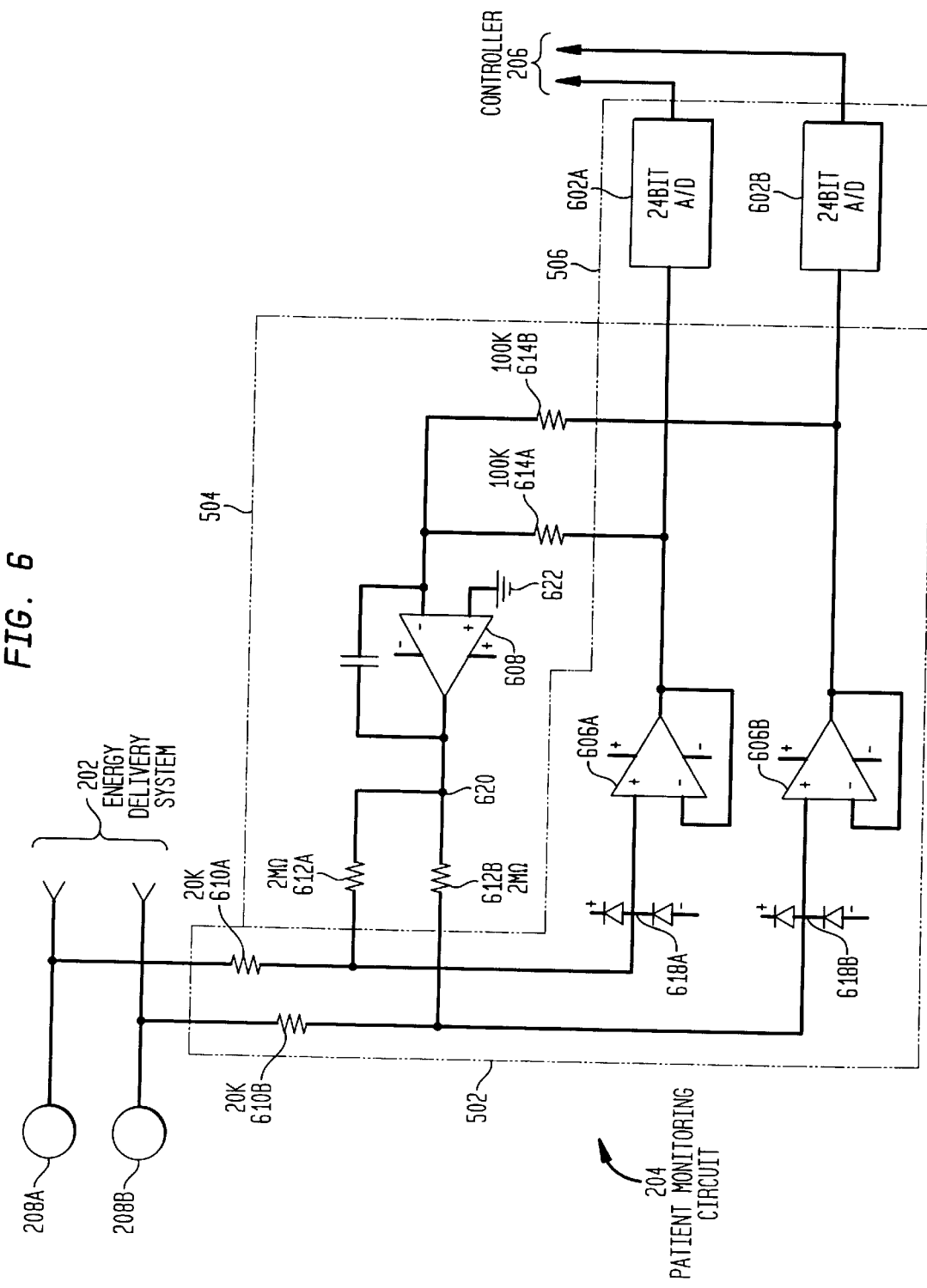
FIG. 6 is a detailed schematic diagram of one embodiment of patient monitoring circuit illustrated in FIG. 5.

Patient monitoring circuit 204, as noted, provides controller 206 with a digital ECG signal. Patient monitoring circuit 204 is a DC coupled measurement circuit with a dynamic range to digitize the DC offset voltage along with the monitored EDG signal resolution to provide relatively quick recovery following a defibrillation event. FIG. 5 is a high-level block diagram of the primary components of patient monitoring circuit 204. FIG. 6 is a more detailed schematic diagram of one implementation of patient monitoring circuit 204. Referring to FIG. 5, patient monitoring circuit 204 includes a buffer amplifier circuit 502 that buffers sensed ECG signal prior to providing them to A/D converter 506. A common mode cancellation circuit 504 is a feedback circuit that dynamically compensates for the voltage difference between the patient voltage and the voltage of monitoring circuit 204. Analog-to-digital (A/D) converter 506 that digitizes the ECG signal for use by controller 206.

There are many implementations of buffer amplifier circuit 502, one of which is illustrated in FIG. 6. Referring to FIG. 6, buffer amplifier circuit 502 includes a buffer amplifier 606 connected to each electrode 208. Specifically, buffer amplifier 606A is electrically connected to electrode 208A while buffer amplifier 606B is electrically connected to electrode 208B. Interposed between buffer amplifier 606 and corresponding electrode 208 is a protection resistor 610A, 610B and protection diodes 618A, 618B to protect corresponding buffer amplifiers 606A, 606B. Buffer amplifiers 606 buffer the ECG voltage signal before applying it to A/D converter 506. A/D converter 506 is described in detail below. It should be appreciated, however, that the design and component selection of buffer amplifier circuit 502 is considered without the purview of those of ordinary skill in the art and is not described further herein.

As noted, patient monitoring circuit 204 also includes a common mode cancellation circuit 504. Common mode cancellation circuit 504 minimizes common mode noise without degrading substantially the differential mode impedance of monitoring circuit 204. As shown in FIG. 6, common mode cancellation circuit 504 is connected in parallel with buffer amplifier circuit 502.

A common objective is to provide an ECG measurement device that has a very high input impedance to minimize the flow of current to the measurement device and the concomitant voltage drop across the high impedance patient/electrode interface. Common mode cancellation circuit 504 includes a resistor 612 connected to each input line into buffer amplifier circuit 502 from electrode 208. Resistors 612A and 612B are connected at a common node 620. The input impedance that a differential voltage across electrodes 208 sees is determined by the values of resistors 612A and 612B. In the embodiment illustrated in FIG. 6, these are both 2-megohm resistors, and the differential impedance is 4-megohm.

As is well known, the voltage of a patient is different from, and may vary relative to, the reference voltage of patient monitoring circuit 204. In this illustrative embodiment, the reference voltage is ground signal 622 applied to the positive input of operational amplifier 608. The difference between this reference voltage and the common mode voltage is reflected in a change in the signal output by buffer amplifiers 606. This signal is provided as a feedback signal to common mode cancellation circuit 504 through resistors 614A and 614B. In the illustrative embodiment, resistors 614 are both 100K resistors. The opposing end of resistors 614 are electrically connected to each other and to the negative input of operational amplifier 608. Thus, resistors 614 are in parallel, and the resulting current is presented to the negative input of operational amplifier 608 and the 100 $\mu$F capacitor 616. When operational amplifier 608 detects a difference between reference voltage 622 and the monitored patient voltage, the operational amplifier 608 driving a current through the 2-megohm resistors 612 sufficient to cancel the difference voltage. Thus, common mode cancellation circuit 504 provides high differential impedance to prevent distortion of ECG signal and a low common mode impedance that stabilizes patient voltage relative to the monitoring circuit 204.

As noted, the output of buffer amplifier circuit 502 is presented to A/D converter 506 to be digitized for controller 206. In this exemplary embodiment, A/D converter 506 includes two 24-bit AID converters 602A, 602B each converting the analog signal produced by a buffer amplifier 606. As noted, the present invention generates two or more successive electrical shocks based on the monitored ECG signal. The successive shock must occur quickly. Accordingly, 24-bit converters 602 are preferably implemented in components that can recover quickly after a defibrillation event. For example, in one embodiment, A/D converters 602 digitize the ECG signal in approximately 50 ms following a defibrillation shock. To achieve this, the selected 24-bit A/D converters 602 has a significant dynamic range to account for shifts in DC offset voltage and which can digitize the full ECG signal range at the desired resolution.

It should be understood that other implementations could be used in other applications. For example, buffer amplifier circuit 502 could include a difference amplifier that generates a single signal that is digitize by a single A/D converter.

Controller 206 implements conventional ECG signal processing and implements the defibrillation process of the present invention. In one embodiment, the energy of each low energy pulse delivered in accordance with the present invention is between approximately 30–70 Joules. In alternative embodiments, other low energy pulses can be implemented. For example, in one embodiment the low energy pulses delivery between approximately 40–60 Joules, while in a further embodiment, 50 Joules. The methodology of the present invention can be implemented as shown in FIGS. 1A or 1B or some variation thereof or equivalent alternatives thereto.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A method for defibrillating a fibrillating heart comprising:
   applying a first low energy current pulse to the heart;
   detecting a reinitiate fibrillation of the heart subsequent to said application of said first low energy current pulse; and
   applying, at the onset of reinitiate fibrillation, a second low energy current pulse.

2. The method of claim 1, further comprising:
   detecting a reinitiate fibrillation of the heart subsequent to said application of said second low energy current pulse; and
   applying, at the onset of reinitiate fibrillation, a third low energy current pulse.

3. The method of claim 2, further wherein said detecting and applying are repeated until the heart no longer experiences reinitiate fibrillation.

4. An external defibrillator to defibrillate a patient's fibrillating heart comprising:
  an energy delivery system constructed and arranged to deliver sequentially two or more low energy electric shocks to a patient through at least two electrodes applied to the patient;
  a patient monitoring circuit constructed and arranged to monitor the patient's heart rhythm; and
  a controller that determines whether the heart is fibrillating and causes said energy delivery system to apply a first low energy electric shock upon detection of an initial fibrillation, and to apply a second low energy electric shock upon detection of a reinitiate fibrillation.

5. The external defibrillator of claim 4, wherein said patient monitoring circuit receives analog ECG signals from sensors integrated in said defibrillating electrodes, and provides said controller with a digitized ECG signal.

6. The external defibrillator of claim 4, wherein said energy delivery system comprises:
  a plurality of charge capacitors each for storing energy to be delivered in a single low energy current pulse;
  a high voltage charge circuit configured to receive power from a power source and to charge said plurality of capacitors; and
  a multiple charge delivery circuit that independently connects each of said plurality of capacitors to said electrodes to effect delivery of multiple low energy current pulses.

7. The external defibrillator of claim 6, wherein said plurality of charge capacitors comprise:
  a first capacitor having a first capacity; and
  a second capacitor having a second capacity substantially the same as said first capacity.

8. The external defibrillator of claim 6, wherein said high voltage charge circuit charges said plurality of capacitors simultaneously.

9. The external defibrillator of claim 6, wherein said patient monitoring circuit is a DC coupled monitoring circuit constructed and arranged to monitor said ECG signals in a sufficiently short time interval following a defibrillation event that said patient monitoring circuit accurately detects a reinitiate fibrillation occurring subsequent to said defibrillation event.

10. The external defibrillator of claim 4, wherein said defibrillator is a portable external defibrillator.

11. The external defibrillator of claim 4, wherein said low energy current pulse is biphasic current pulse.

12. The external defibrillator of claim 4, wherein said low energy current pulse is monophasic current pulse.

13. An external defibrillator to defibrillate a patient's fibriliating heart, comprising:
  an energy delivery system constructed and arranged to deliver sequentially two or more low energy shocks to a patient through at least two electrodes applied to the patient,
    wherein said energy delivery system comprises:
      a plurality of charge capacitors each for storing energy to be delivered in a single low energy current pulse, said plurality of charge capacitors comprising a first capacitor having a first capacity and a second capacitor having a second capacity substantially the same as said first capacity,
      a high voltage charge circuit configured to receive power from a power source and to charge said plurality of capacitors; and
      a multiple charge delivery circuit that independently connects each of said plurality of capacitors to said electrodes to effect delivery of multiple low energy current pulses;
  a patient monitoring circuit constructed and arranged to monitor the patient's heart rhythm; and
  a controller that determines whether the heart is fibrillating and causes said energy delivery system to apply a first low energy shock upon detection of an initial fibrillation, and to apply a second low energy electric shock upon detection of a reinitiate fibrillation,
    wherein said first capacity and said second capacity is approximately 100 uf.

14. An external defibrillator to defibrillate a patient's fibrillating heart, comprising:
  an energy delivery system constructed and arranged to deliver sequentially two or more low energy shocks to a patient through at least two electrodes applied to the patient,
    wherein said energy delivery system comprises:
      a plurality of charge capacitors each for storing energy to be delivered in a single low energy current pulse;
      a high voltage charge circuit configured to receive power from a power source and to charge said plurality of capacitors; and
      a multiple charge delivery circuit that independently connects each of said plurality of capacitors to said electrodes to effect delivery of multiple low energy current pulses;
  a patient monitoring circuit constructed and arranged to monitor the patient's heart rhythm; and
  a controller that determines whether the heart is fibrillating and causes said energy delivery system to apply a first low energy shock upon detection of an initial fibrillation, and to apply a second low energy electric shock upon detection of a reinitiate fibrillation,
    wherein said multiple charge delivery circuit controls said electrical connection of each said capacitor to said electrodes to cause said first and second low energy current pulses to deliver substantially different energy.

15. An external defibrillator to defibrillate a patient's fibrillating heart, comprising:
  an energy delivery system constructed and arranged to deliver sequentially two or mare low energy shocks to a patient through at least two electrodes applied to the patient,
    wherein said energy delivery system comprises:
      a plurality of charge capacitors each for storing energy to be delivered in a single low energy current pulse;
      a high voltage charge circuit configured to receive power from a power source and to charge said plurality of capacitors; and
      a multiple charge delivery circuit that independently connects each of said plurality of capacitors to said electrodes to effect delivery of multiple low energy current pulses,
  a patient monitoring circuit constructed and arranged to monitor the patient's heart rhythm; and
  a controller that determines whether the bean is fibrillating and causes said energy delivery system to apply a first low energy shock upon detection of an initial fibrillation, and to apply a second low energy electric shock upon detection of a reinitiate fibrillation,
    wherein said multiple charge delivery circuit is implemented as two H-bridge circuits each electrically connecting one of said plurality of capacitors to said defibrillation electrodes.

16. The external defibrillator of claim 15, wherein said energy delivered by said low energy current pulse is between approximately 30–70 Joules.

17. An external defibrillator to detibrillate a patient's fibrillating heart, comprising:
- an energy delivery system constructed and arranged to deliver sequentially two or more low energy shocks to a patient through at least two electrodes applied to the patient,
  - wherein said energy delivery system comprises:
    - a plurality of charge capacitors each for storing energy to be delivered in a single low energy Current pulse;
    - a high voltage charge circuit configured to receive power from a power source and to charge said plurality of capacitors; and
    - a multiple charge delivery circuit that independently connects each of said plurality of capacitors to said electrodes to effect delivery of multiple low energy current pulses;
- a patient monitoring circuit constructed and arranged to monitor the patient's heart rhythm;
  - wherein said patient monitoring circuit is a DC coupled monitoring circuit constructed and arranged to monitor said ECG signals in a sufficiently shod time interval following a defibrillation event that said patient monitoring circuit accurately detects a reinitiate fibrillation occurring subsequent to said defibrillation event, and further comprises:
    - an analog-to-digital converter that digitizes the ECG signal for use by said controller;
    - a buffer amplifier circuit connected to said electrodes, configured to buffer ECO signals prior to providing them to said analog-to-digital converter; and
    - a common mode cancellation circuit connected in parallel with said buffer amplifier circuit, configured to minimize common mode noise without degrading substantially a differential mode impedance of said patient monitoring circuit, and
- a controller that determines whether the heart is fibrillating and causes said energy delivery system to apply a first low energy shock upon detection of an initial fibrillation, and to apply a second low energy electric shock upon detection of a reinitiate fibrillation.

18. The external defibrillator of claim 17, wherein said portable external defibrillator is an AED.

19. An external defibrillator to defibrillate a patient's fibrillating heart, comprising:
- an energy delivery system constructed and arranged to deliver sequentially two or more low energy shocks to a patient through at least two electrodes applied to the patient,
- a patient monitoring circuit constructed and arranged to monitor the patient's heart rhythm; and
- a controller that determines whether the bean is fibrillating and causes said energy delivery system to apply a first low energy shock upon detection of an initial fibrillation, and to apply a second low energy electric shock upon detection of a reinitiate fibrillation,
- wherein each of said plurality of charge capacitors comprises two or more physically separate capacitors electrically connected in series to produce an equivalent capacitance.

20. A transthoracic electrical defibrillation system that effectively defibrillates a fibrillating heart by delivering two successive low energy electrical shocks to the fibrillating heart with the second such low energy shock being applied at the onset of reinitiate fibrillation.

* * * * *